United States Patent [19]

Cinberg et al.

[11] Patent Number: 5,421,325
[45] Date of Patent: Jun. 6, 1995

[54] ENDOTRACHEAL TUBE ASSEMBLY AND RELATED METHOD

[76] Inventors: James Z. Cinberg, 167 N. Ridgewood Rd., South Orange, N.J. 07079; Peter J. Wilk, 185 W. End Ave., New York, N.Y. 10023

[21] Appl. No.: 174,398

[22] Filed: Dec. 28, 1993

Related U.S. Application Data

[63] Continuation-in-part of Ser. No. 876,516, Apr. 30, 1992, Pat. No. 5,273,029.

[51] Int. Cl.⁶ .................................................. A61M 16/00
[52] U.S. Cl. ............................ 128/200.26; 128/207.14
[58] Field of Search ................... 128/200.26, 207.14, 128/207.15; 604/99, 100

[56] References Cited

U.S. PATENT DOCUMENTS

| | | | |
|---|---|---|---|
| 3,373,735 | 3/1968 | Gallagher | 128/207.18 |
| 3,402,717 | 9/1968 | Doherty | 604/99 |
| 4,266,550 | 5/1981 | Bruner | 128/207.15 |
| 4,361,107 | 11/1982 | Gereg | 604/100 |
| 4,552,558 | 11/1985 | Muto | 604/100 |
| 4,617,015 | 10/1986 | Foltz | 604/100 |
| 4,691,701 | 9/1987 | Williams | 128/207.14 |
| 4,728,499 | 3/1988 | Fehder | 128/207.14 |
| 4,790,327 | 12/1988 | Despotis | 128/207.16 |
| 4,821,710 | 4/1989 | Greunwald et al. | 128/207.14 |
| 4,846,153 | 7/1989 | Berci | 128/6 |
| 4,872,483 | 10/1989 | Shah | 604/100 |
| 4,879,999 | 11/1989 | Leiman et al. | 128/207.14 |
| 4,892,095 | 1/1990 | Nakhgerany | 128/207.14 |
| 4,928,687 | 5/1990 | Lampotang et al. | 128/207.14 |
| 5,211,631 | 5/1993 | Sheaff | 604/100 |
| 5,218,970 | 6/1993 | Turnbull et al. | 128/207.15 |
| 5,263,485 | 11/1993 | Hickey | 604/100 |

Primary Examiner—Edgar S. Burr
Assistant Examiner—Aaron J. Lewis
Attorney, Agent, or Firm—R. Neil Sudol; Henry D. Coleman

[57] ABSTRACT

An endotracheal assembly comprises an endotracheal tube, a malleable obturator inside the tube for enabling a placement of a distal end of the tube into a patient's trachea, and a pressure-sensitive detector mounted to the obturator at a distal end thereof for detecting air or gas pressure above a predetermined threshold exerted against a distal end of the obturator upon placement of the tube with the obturator into the patient. Upon an initial insertion of the tube and the obturator into a patient's trachea and possible manipulation of the tube and the obturator to effectuate a placement of the tube, a compressive pressure is exerted externally on the patient's chest. The compressive pressure forces air out of the patient's lungs and, if the tube and obturator assembly is properly placed, effectuates a change in the condition of the pressure sensor. That change in condition indicates that pressure above a predetermined level was exerted against the detector element.

15 Claims, 2 Drawing Sheets

5,421,325

ENDOTRACHEAL TUBE ASSEMBLY AND RELATED METHOD

CROSS-REFERENCE TO A RELATED APPLICATION

This application is a continuation-in-part of application Ser. No. 07/876,516 filed Apr. 30, 1992, now U.S. Pat. No. 5,273,029.

BACKGROUND OF THE INVENTION

This invention relates to an endotracheal tube placement assembly including an endotracheal tube and an obturator. This invention also relates to the obturator itself and to a method for placing an endotracheal tube with an obturator.

The dangers of improper endotracheal tube placement are well known and include death and disability. In an anesthetized patient, an endotracheal tube is placed to secure the air passageway and enable controlled oxygenation of the patient's lungs. However, if the distal end of the endotracheal tube is positioned in the esophagus rather than the lungs and the condition permitted to continue for even a short interval, brain injury and death can result.

It has been proposed to automatically or semiautomatically detect proper endotracheal tube placement by monitoring the carbon dioxide content of the gases escaping through a positioned endotracheal tube. U.S. Pat. Nos. 4,790,327 to Despotis, 4,821,710 to Greunwald et al., 4,879,999 to Leiman et al., 4,728,499 to Fehder, 4,691,701 to Williams, and 4,928,687 to Lampotang et al. disclose the use of colorimetric carbon dioxide indicators to determine the carbon dioxide content of gases exhaled through a positioned endotracheal tube. All the indicators are disposed at the proximal ends of endotracheal tubes, i.e. closest to the mouth and furthest from the lungs, or on devices connected to the proximal ends of endotracheal tubes. Accordingly, because carbon dioxide is present in exhaled air in a concentration of only 5%, the indicators must be especially sensitive to detect the carbon dioxide content of exhaled gases.

OBJECTS OF THE INVENTION

An object of the present invention is to provide an assembly for facilitating proper endotracheal tube placement.

Another object of the present invention is to provide a method for endotracheal tube placement which uses an indicator other than a carbon-dioxide sensor to enable accurate positioning of an endotracheal tube.

Another, more particular, object of the present invention is to provide an endotracheal tube placement assembly with a pressure sensing indicator for determinign proper tube placement.

A further particular object of the present invention is to provide an improved obturator for use in positioning an endotracheal tube.

These and other objects of the present invention will be apparent from the following descriptions and the attached drawings.

SUMMARY OF THE INVENTION

An endotracheal assembly comprises, in accordance with the present invention, an endotracheal tube, a malleable obturator inside the tube for enabling a placement of a distal end of the tube into a patient's trachea, and a pressure-sensitive detector mounted to the obturator at a distal end thereof for detecting air or gas pressure above a predetermined threshold exerted against a distal end of the obturator upon placement of the tube with the obturator into the patient.

Upon an initial insertion of the tube and the obturator into a patient's trachea and possible manipulation of the tube and the obturator to effectuate a placement of the tube, a compressive pressure is exerted externally on the patient's chest. The compressive pressure forces air out of the patient's lungs and, if the tube and obturator assembly is properly placed, effectuates a change in the condition of the pressure sensor. That change in condition indicates that pressure above a predetermined level was exerted against the detector element.

To detect whether a change in condition of the pressure sensor has occurred, an anaesthesiologist or other user withdraws the obturator and inspects the pressure measurement element. A sufficient change in detector condition indicates proper tube placement. In that case, the obturator is set aside and the surgical operation on the patient proceeds. In the event that the detector evinces no change or change below a preselected threshold, the tube is removed and reinserted into the patient with the same obturator and the same pressure detector or with another pressure detector, whether on the same obturator or another obturator.

Where the same obturator and a different pressure detector is used in a tube reinsertion operation, the original pressure detector is removably attached to the distal end of the obturator. Preferably, means are provided for releasably locking the detector to the distal end of the obturator.

Of course, the tube, the obturator and the detector are preferably sterile prior to the initial insertion. Sterility may be ensured by enclosing the tube and the obturator (as well as the pressure detector) in a removable disposable wrapper.

The pressure detector may take any of many equivalent forms. The detector may have an element which is attached to a frame or holder for motion in a proximal direction relative to the holder. Upon being pressed in the proximal direction by excessive air presure, the movable element locks and cannot return to its original position.

Alternatively, a Castelli membrane may be provided at the distal end of a fluid-filled chamber attached to the obturator. Air forced through the membrane appears as bubbles in the fluid.

An endotracheal tube placement assembly with a pressure detector on an obturator in accordance with the present invention is more reliable than existing devices wherein a carbon dioxide indicator is placed on the endotracheal tube. In those devices, the carbon dioxide indicator is necessarily disposed at the proximal end of the endotracheal tube, where the carbon dioxide is more dispersed and less concentrated than in the lungs.

DETAILED DESCRIPTION

Figure 1:
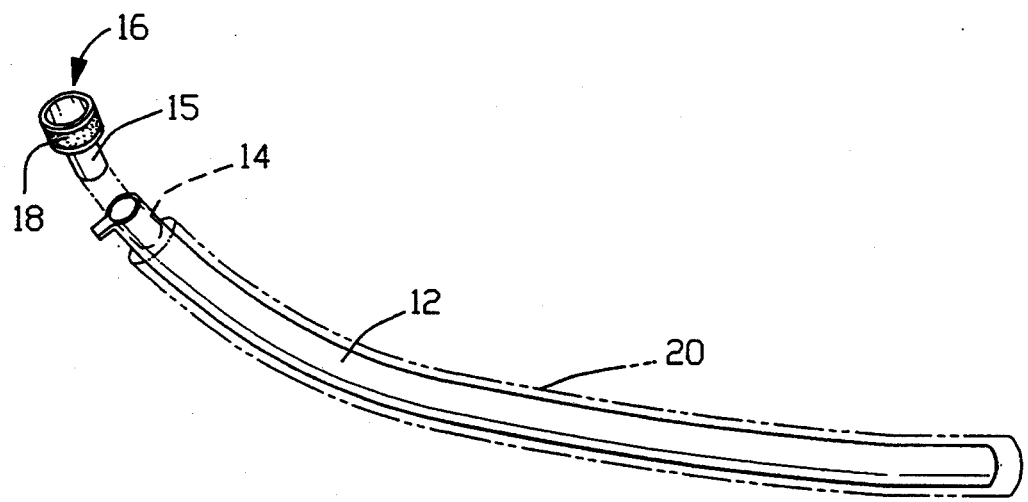
FIG. 1 is a schematic side perspective view of an endotracheal tube assembly.

As illustrated in FIG. 1, an endotracheal tube assembly comprises a malleable obturator 12 proxided at a proximal end with a recess 14 for receiving a plug or finger element 15 of an indicator member 16. Indicator member 16 carries a colorimetric carbon dioxide indicator strip 18.

Obturator 12 is removably inserted into an endotracheal tube 20. The entire assembly may be contained in a sterile envelope or package (not shown) prior to use. Upon removal from the envelope or package, the endotracheal tube assembly of FIG. 1 is inserted into a patient's trachea in the same manner as conventional endotracheal tube assemblies. However, indicator strip 18 is monitored for color change to determine that the distal end of the endotracheal tube 20 has been properly positioned inside the patient's lung.

Figure 2:
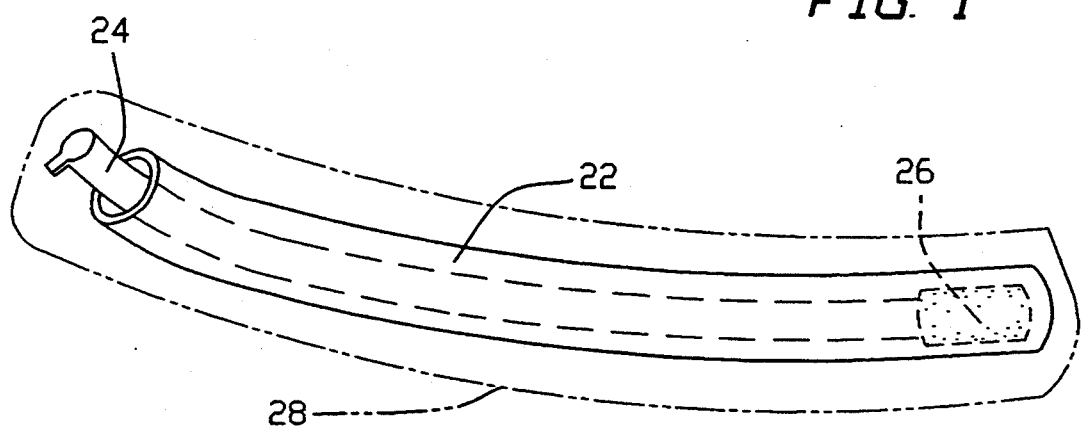
FIG. 2 is a schematic side perspective view of another endotracheal tube assembly.

As depicted in FIG. 2, another endotracheal tube assembly comprises an endotracheal tube 22 in which a malleable tube placement obturator 24 is slidably disposed. Permanently attached to a distal end of obturator 24 is a colorimetric carbon dioxide indicator 26, for example, in the form of a strip inserted into an annular recess (not shown) in a distal end portion of obturator 24. Prior to use, tube 22 and obturator 24 are preserved in a sterile condition by a disposable envelope 28.

Figure 3:
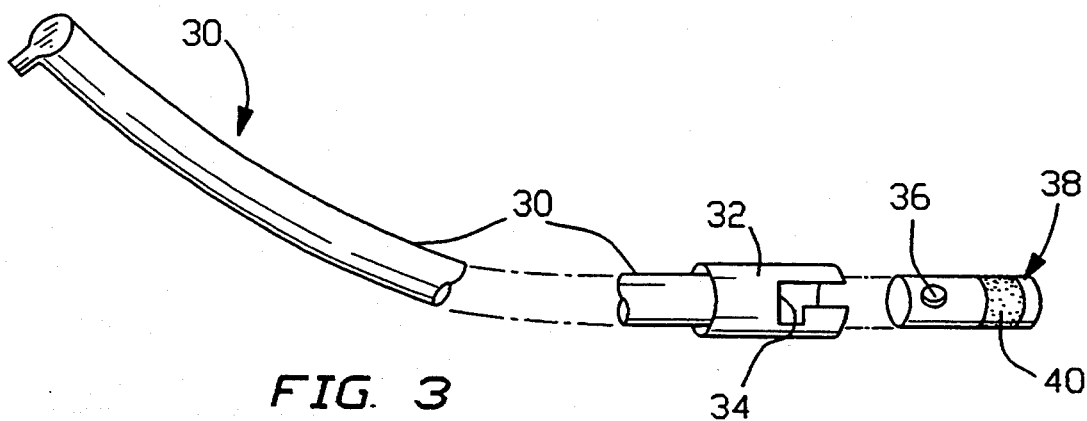
FIG. 3 is a schematic side perspective view of an obturator for use in an endotracheal tube assembly in accordance with the present invention.

FIG. 3 shows another obturator 30 utilizable in an endotracheal tube assembly for facilitating the placement of the tube (e.g., tube 22 in FIG. 2). Obturator 30 is provided at a distal end with an enlarged hollow head 32 provided with an L-shaped slot 34 for receiving a protuberance 36 on an indicator member 38 during insertion of the indicator member into head 32. Indicator member 38 carries a colorimetric carbon dioxide indicator strip 40.

In placing endotracheal tube 22 with obturator 24 or 30, the endotracheal tube is inserted into a patient's trachea. Obturator 24 or 30 and tube 22 are manipulated from outside the patient's body to effectuate a placement of the tube so that a distal end of the tube is positioned in the patient's lung. Upon a placement of tube 22 with obturator 24 or 30, the obturator is withdrawn from tube 22. Colorimeteric carbon dioxide indicator strip 26 or 40 is then inspected to determine whether a distal end of tube 22 is properly placed in the patient's lung. A color change of indicator strip 26 or 40 indicates proper placement.

If it is determined via the color of indicator strip 26 or 40 that tube 22 is improperly placed, tube 22 is removed and again inserted into the patient's trachea. Alternatively, a new tube may be employed. A reinsertion of the original endotracheal tube 22 may be implemented with the same obturator 24 or 30 and indicator strip 26 or 40, provided that the color thereof has not changed so much as to render the strip useless for further determinations. Alternatively, in the case of obturator 30, a new indicator member 38 may be attached to the distal end of obturator 30. In the case that the color of strip 26 of obturator 24 has changed too much for re-use, a new obturator may be used.

It is to be noted that, in contrast to the embodiments of FIGS. 2 and 3, the embodiment of FIG. 1 requires that the obturator 12 is somewhat thinner than the inner diameter of endotracheal tube 20 to allow exhaled gases to escape through the tube and around indicator strip 18 at the proximal end of obturator 12. The endotracheal obturators 24 and 30 of FIGS. 2 and 3 may snugly fit inside endotracheal tube 22. Accordingly, the embodiments of FIGS. 2 and 3 are preferred over the embodiment of FIG. 1.

Moreover, obturator 24 of FIG. 2 is preferred to obturator 30 of FIG. 3 insofar as indicator 26 is permanently attached to the distal end of the obturator, thereby ensuring that the indicator is not inadvertently dislodged during use and lost in the trachea or the lung. Obturator 24 may be sold separately in its own disposable sterile wrapper.

Figure 4A:
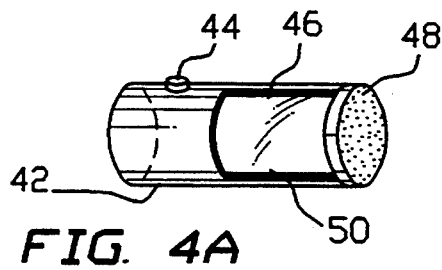
FIGS. 4A and 4B are schematic side perspective views of a pressure detector module attachable to a distal end of the obturator of FIG. 3, in accordance with the present invention, showing the detector before and after a pressure measurement operation during an endotracheal tube placement procedure.

As illustrated in FIG. 4A, indicator member 38 (FIG. 3) may be replaced by a pressure-sensitive detector module 42 removably mounted to head 32 at the distal end of obturator 30. Pressure-sensitive detector module 42 includes a protuberance 44 insertable into L-shaped slot 34 (FIG. 3) of head element 32 for releasably locking the detector module to obturator 30. Detector module 42 encloses a chamber 46 which contains a viscous liquid. Chamber 46 is defined at a distal end of detector module 42 by a Castelli membrane 48. In addition, detector module 42 is provided with a transparent wall section or window 50 for enabling an inspection of the liquid in chamber 46.

Figure 4B:
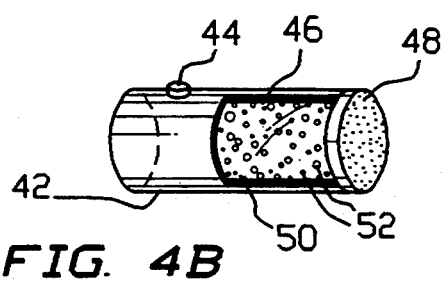

Castelli membrane 48 and the liquid chamber 46 cooperate to detect air or gas pressure above a predetermined threshold exerted on membrane 48 upon placement of obturator 38 and an associated endotracheal tube 20 (FIGS. 1 and 2) with the obturator into a patient. Air is forced under pressure through membrane 48 to form bubbles 52 in the liquid in chamber 46, as shown in FIG. 4B.

Upon an initial insertion of an endotracheal tube and obturator 30 into a patient's trachea and possible manipulation of the tube and the obturator to effectuate a placement of the tube, a compressive pressure is exerted externally on the patient's chest. This compressive pressure may be accomplished manually by pressing sufficiently sharply with hands on the patient's rib cage. The compressive pressure forces air out of the patient's lungs and, if the tube and obturator assembly is properly placed, forces air through membrane 48 to form bubbles 52 in the liquid in chamber 46.

Upon the pressing of the patient's chest, obturator 30 is withdrawn with pressure-sensitive detector module 42. If bubbles 52 are present in chamber 46, intubation is deemed adequate and a surgical operation is commenced. If there are no bubbles in chamber 46 (FIG. 4A), the tube is not properly placed and is therefore withdrawn to effectuate another placement. The same obturator 30 and the same pressure-sensitive detector module 42 may be used in the subsequent insertion operation. Alternatively, module 42 may be removed and replaced with another module.

Figure 5B:
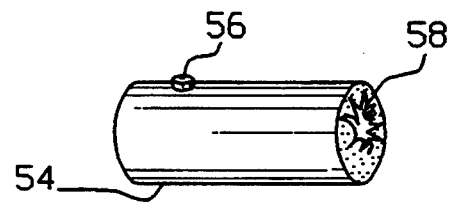
FIGS. 5A and 5B are schematic side perspective views of another pressure detector module attachable to a distal end of the obturator of FIG. 3, in accordance with the present invention, showing the detector before and after a pressure measurement operation during an endotracheal tube placement procedure.
Figure 5A:
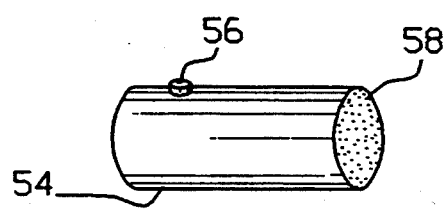

As depicted in FIG. 5A and FIG. 5B, another pressure-sensitive detector module 54 removably mountable to head 32 at the distal end of obturator 30 includes a locking protuberance 56 and is provided at a distal end with a film 58 which is ruptured upon the application of a sufficiently powerful blast of air.

As described hereinabove with reference to FIGS. 4A and 4B, a compressive pressure is exerted externally on a patient's chest upon a placement of an endotracheal tube and obturator 30 with pressure-sensitive detector module 54 into the patient. This compressive pressure forces air out of the patient's lungs and, if the tube and obturator assembly is properly placed, forces air against film 58 to rupture that film, as indicated in FIG. 5B. The obturator is withdrawn to enable inspection of the film 58 following the application of compressive chest pressure.

Figure 6A:
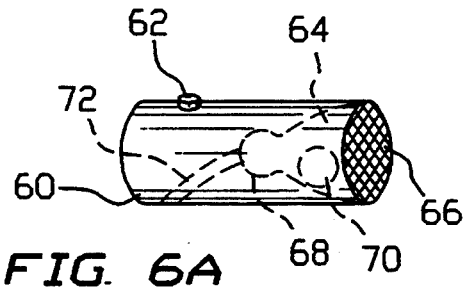
FIGS. 6A and 6B are schematic side perspective views of a further pressure detector module attachable to a distal end of the obturator of FIG. 3, in accordance with the present invention, showing the detector before and after a pressure measurement operation during an endotracheal tube placement procedure.
Figure 6B:
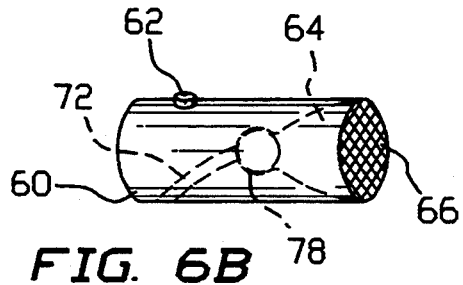

As depicted in FIGS. 6A and 6B, another pressure-sensitive detector module 60 removably mountable to head 32 at the distal end of obturator 30 includes a locking protuberance 62 and is provided at a distal end with a substantially cone-shaped recess 64 bounded by a screen 66 on a distal side and having a recess extension 68 on a proximal side. A ball 70 of a light material (e.g., styrofoam) is disposed in cone-shaped recess 64.

Upon a placement of an endotracheal tube with obturator 30 and pressure-sensitive detector module 60 and upon subsequent application of a compressive pressure to the patient's chest, the obturator is withdrawn to enable inspection of the ball 70 to determine whether the ball has become lodged in recess extension 68 (FIG. 6B). A conduit 72 extends from extension 68 to facilitate the flow of air through recess 64.

Figure 7:
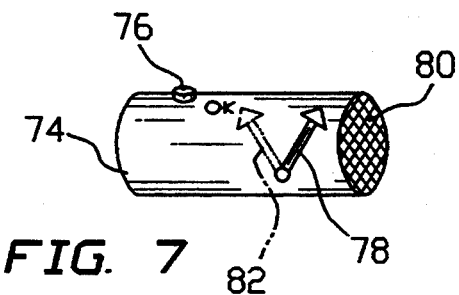
FIG. 7 is a schematic side perspective view of yet another pressure detector module attachable to a distal end of the obturator of FIG. 3, in accordance with the present invention, showing the detector before and after a pressure measurement operation during an endotracheal tube placement procedure.

As illustrated in FIG. 7, a further pressure-sensitive detector module 74 removably mountable to head 32 at the distal end of obturator 30 includes a locking protuberance 76 and is provided at a distal end with a pivoting valve member (not shown) connected to an external indicator arm 78. Upon the exertion of pressure against the valve through a screen 80 on the distal side of the module 74, the indicator arm pivots from a pre-insertion position (solid lines) to a position 82 indicating that proper tube placement has been effectuated.

Although the invention has been described in terms of particular embodiments and applications, one of ordinary skill in the art, in light of this teaching, can generate additional embodiments and modifications without departing from the spirit of or exceeding the scope of the claimed invention. It is to be noted that the particular structure for releasably locking a pressure detector module to the distal end of an endotracheal tube obturator may take any of a number of equivalent forms. For example, a force lock fit or a snap-lock detent are substitutable for L-shaped slot 34 and protuberance 36.

A colorimetric indicator strip in accordance with the present invention may be enclosed by a semipermeable membrane for preventing particles of the indicator from entering air passing through the endotracheal tube while enabling penetration of carbon dioxide molecules to the indicator. Of course, replaceable indicator members 16 and 38 may be enclosed by separate sterile packages for shipment and handling prior to use during surgery.

It is to be understood that an obturator for endotracheal tube placement in accordance with the present invention may incorporate both a carbon dioxide detector and a pressure detector at the distal end.

Accordingly, it is to be understood that the drawings and descriptions herein are proferred by way of example to facilitate comprehension of the invention and should not be construed to limit the scope

What is claimed is:

1. An endotracheal assembly comprising:
   an endotracheal tube;
   a malleable obturator inside said tube for enabling a placement of a distal end of said tube into a patient's trachea; and
   pressure-sensitive detector means mounted to said obturator at a distal end thereof for detecting air or gas pressure above a predetermined threshold exerted against a distal end of said obturator upon placement of said tube with said obturator into the patient.

2. The assembly defined in claim 1 wherein said detector means is removably attached to said distal end of said obturator.

3. The assembly defined in claim 2, further comprising means for releasably locking said detector means to said distal end of said obturator.

4. The assembly defined in claim 1 wherein said tube, said obturator and said detector means are sterile, further comprising a removable disposable wrapper enclosing said tube and said obturator for purposes of maintaining said tube, said obturator and said detector means in a sterile condition.

5. A device for determining proper placement of an endotracheal tube, comprising:
   a malleable obturator insertable inside an endotracheal tube; and
   pressure-sensitive detector means mounted to said obturator at a distal end thereof for detecting air or gas pressure above a predetermined threshold exerted against a distal end of said obturator upon placement of an endotracheal tube, with said obturator disposed therein, into the patient.

6. The device defined in claim 5 wherein said detector means is removably attached to the distal end of said obturator.

7. The device defined in claim 6, further comprising means for releasably locking said detector means to the distal end of said obturator.

8. The device defined in claim 5, further comprising means for releasably locking said detector means to said obturator.

9. The device defined in claim 5 wherein said obturator and said detector means are sterile, further comprising a removable disposable wrapper enclosing said obturator and said detector means for purposes of maintaining said obturator and said detector means in a sterile condition.

10. A method for placing an endotracheal tube, comprising the steps of:
    initially inserting into a patient's trachea an endotracheal tube longitudinally traversed at least partially by an obturator made of a malleable material;
    manipulating said tube and said obturator to effectuate a placement of said tube;

upon a placement of said tube with said obturator, exerting compressive pressure externally on the patient's chest;

upon exertion of compressive pressure on the patient's chest, withdrawing said obturator; and inspecting a pressure measurement element mounted to a distal end of said obturator to determine the whether said distal end of said obturator has been exposed to a gaseous pressure in excess of a predetermined level, thereby determining that a distal end of said tube is properly placed in the patient.

11. The method defined in claim 10, further comprising the steps of:

removing said tube upon determining, via a condition of said pressure measurement element, that said tube is improperly placed; and again inserting into the patient's trachea an endotracheal tube longitudinally traversed at least partially by an obturator made of a malleable material.

12. The method defined in claim 11 wherein the obturator utilized in said step of again inserting is a different obturator than that obturator used in said step of initially inserting.

13. The method defined in claim 11 wherein the endotracheal tube utilized in said step of again inserting is the same tube used in said step of initially inserting.

14. The method defined in claim 13, further comprising the step of leaving said endotracheal tube inside the patient upon determining, via said condition of said pressure measurement element, that said tube is properly placed.

15. The method defined in claim 11 wherein the endotracheal tube and obturator utilized in said step of again inserting are the same tube and obturator used in said step of initially inserting.

* * * * *